(12) United States Patent
Manley

(10) Patent No.: US 8,604,045 B2
(45) Date of Patent: Dec. 10, 2013

(54) PYRIMIDYLAMINOBENZAMIDE DERIVATIVES FOR TREATMENT OF NEUROFIBROMATOSIS

(71) Applicant: Novartis AG, Basel (CH)

(72) Inventor: Paul W. Manley, Arlesheim (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/706,249

(22) Filed: Dec. 5, 2012

(65) Prior Publication Data
US 2013/0123290 A1    May 16, 2013

Related U.S. Application Data

(63) Continuation of application No. 12/730,590, filed on Mar. 24, 2010, now abandoned, which is a continuation of application No. 12/095,956, filed as application No. PCT/EP2006/069335 on Dec. 5, 2006, now abandoned.

(60) Provisional application No. 60/742,781, filed on Dec. 6, 2005.

(51) Int. Cl.
*A61K 31/505* (2006.01)
*A61K 31/415* (2006.01)

(52) U.S. Cl.
USPC .......................................... 514/275; 514/393

(58) Field of Classification Search
USPC ................................................. 514/375, 393
See application file for complete search history.

(56) References Cited

FOREIGN PATENT DOCUMENTS

| WO | WO 2004/005281 | 1/2004 |
|---|---|---|
| WO | WO 2005/039586 | 4/2005 |
| WO | WO 2005/049032 | 6/2005 |
| WO | WO 2006/079539 | 8/2006 |

OTHER PUBLICATIONS

Giles, Frances, "A Phase I/II study of AMN107, a Novel Aminopyrimidine Inhibitor of Bcr-Abl, on a Continuous Daily Dosing Schedule in Adult Patients (pts) with Imatinib-Resistant Advanced Phase Chronic Myeloid Leukemia (CML) or Relapsed/Refractory Philadelphis Chromosome (Ph+) Acute Llymphocytic Leukemia (ALL)", Blood, vol. 104, No. 11, Part 1, Abstract 22, Nov. 2004.
Badache et al., "Expression of Kit neurofibromin-deficient human Schwann cells: role in Schwann cell hyperplasia associated with Type 1 Neurofibromatosis", Oncogene, vol. 17, pp. 795-800, 1998.
David Charles: "Benign Brain Tumors", MedicineNet.com, http://www.medicinenet.com/script/main/art.asp?articlekey-86535, 2008, accessed Aug. 21, 2009.
Mass General Hopsoital for Children: "Neurofibromatosis", http://www.massgeneral.org/children/adolescenthealth/articles/aa_neurofibromatosis.aspx, 2009, accessed Aug. 21, 2009.
Mukherjee Joydeep: Human schwannomas express activated platelet-derived growth factor receptors and -kit and are growth inhibited by gleevec (imatinib mesylate), Cancer Research 69: (12), pp. 5099-5107, Jun. 15, 2009.
Badache A et al. "Expression of Kit in neurofibromin-deficient human Schwann cells: role in Schwann cell hyperplasia associated with Type 1 Neurofibromatosis", Oncogene vol. 17, No. 6, pp. 795-800 (1998).
Weisberg E et al. "Characteriztion of AMN107, a selective inhibitor of native and mutant Bcr-Abl", Cancer Cell, vol. 7, No. 2, pp. 129-141 (2005).
Holtkamp, N et al, "Mutation and expression of PDGFRA and KIT in malignant peripheral nerve sheath tumors, and its implications for imatinib sensitivity", Cancinogenesis, vol. 27, No. 3, pp. 664-671(2006).
Stover E et al. "The small molecule tyrosine, kinase inhibitor AMN107 inhits TEL-PDGFRβ and FIP1L1-PDGFRα in vitro and in vivo", Blood, vol. 106, No. 9, pp. 3206-3213 (2005).
Manley P et al. "Advances in the structural biology, design and clinical development of Bcr-Abl kinase inhibitors for the treatment of chronic myeloid leukaemia", Biochimica et Biophysica Acta, vol. 1754, pp. 3-13 (2005).
Weisberg et al. "Effects of PKC412 Nilotinib and Imatinib Against GIST-Associated PDGFRA Mutants With Differential Imatinib Sensitivity", Gastroenterology vol. 131, pp. 1734-1742 (2006).

*Primary Examiner* — Paul Zarek
(74) *Attorney, Agent, or Firm* — Stephen Johnson

(57) ABSTRACT

The present invention relates to the use of pyrimidylaminobenzamide derivatives for the preparation of a drug for the treatment of non-cancerous, benign brain tumors, especially for the curative and/or prophylactic treatment of NF, and to a method of treating non-cancerous, benign brain tumors, especially for the curative and/or prophylactic treatment of NF.

2 Claims, No Drawings

PYRIMIDYLAMINOBENZAMIDE DERIVATIVES FOR TREATMENT OF NEUROFIBROMATOSIS

This application is a continuation of U.S. application Ser. No. 12/730,590 filed Mar. 24, 2010, which is a continuation of U.S. application Ser. No. 12/095,956 filed Jun. 3, 2008, which is a National Stage of International Application No. PCT/EP06/069335 filed on Dec. 5, 2006, which claims benefit of U.S. Provisional Application No. 60/742,781, filed Dec. 6, 2005, the entire disclosure of which are herein incorporated by reference.

SUMMARY OF THE INVENTION

The present invention relates to the use of pyrimidylaminobenzamide derivatives for the treatment of, and preparation of a drug for the treatment of, non-cancerous, benign brain tumors, especially for the curative and/or prophylactic treatment of meningiomas, schwannomas, craniopharyngiomas, dermoids, epidermoids, hemangioblastomas, choroid plexus papillomas and pineal region tumors; especially those tumors associated with neurofibromatosis types 1 and 2, and tumors occurring along the skull base.

BACKGROUND OF THE INVENTION

Neurofibromatosis (NF) is a genetic disorder that affects the bone, soft tissue, skin and nervous system. It is classified into neurofibromatosis type 1 (NF1) and neurofibromatosis type 2 (NF2), occurring in about 1 in 3,000 and 1 in 50,000 births, respectively. The disorders occur as a result of genetic defects, with NF1 resulting from a mutation on a gene located on chromosome 17 and NF2 on chromosome 22.

NF1, also known as von Recklinghausen Disease, is a hereditary disease seen in approximately 1 in 4,000 live births in the U.S. NF1 is characterized by a triad of café-au-lait spots (skin discolorations), cutaneous neurofibromata and iris Lisch nodules. Other features of the disorder may include skeletal dysplasia, vascular dysplasias, learning disabilities, seizures and other tumors of the neural crest origin, such as pheochromocytomas. In addition, about 10-15% of NF1 patients have low-grade astrocytomas, and less commonly, ependymoas or meningiomas.

NF2, is characterized by bilateral vestibular schwannomas with associated symptoms of tinnitus, hearing loss and balance dysfunction. Other findings include schwannomas of other cranial and peripheral nerves, meningiomas and juvenile posterior subcapsular contaract.

Both forms of NF are characterized by the growth of benign tumors called neurofibromas. These tumors can grow anywhere in the body where there are nerve cells. This includes nerves just under the surface of the skin, as well as nerves deeper within the body, spinal cord and/or brain. Neurofibromas usually originate in peripheral nerve fibres.

In NF1, neurofibromas most commonly grow on the skin or on the nerve to the eye. A tumor that grows on the nerve to the eye is called an optic glioma, and if it grows large enough can cause problems with vision, including blindness.

If untreated, a neurofibroma can cause severe nerve damage leading to loss of function to the area stimulated by that nerve, such as malformation of the long bones, curvature of the spine, short stature and growth hormone deficiency. Tumors on the optic nerve can cause visual loss, on the gastrointestinal tract may cause bleeding or obstruction, on the brain may lead to learning difficulties (speech problems), behavioural problems (learning disabilities or mental retaration), hearing problems, increased risk of epilepsy.

Currently, the only treatment available for NF is surgery.

The NF1 gene encodes neurofibromin, a tumor suppressor postulated to function in part as a Ras GTPase-activating protein. Ras is a downstream component of PDGFR and Kit receptors signalling, which have been found to be upregulated in NF1-positive cells.

As an inhibitor of both PDGFR and Kit receptor signalling, AMN107 has the potential to be of benefit in the treatment of NF.

SUMMARY OF THE INVENTION

The present invention relates to the use of pyrimidylaminobenzamide compounds of formula (I) (hereinafter: "PYRIMIDYLAMINOBENZAMIDE DERIVATIVES"):

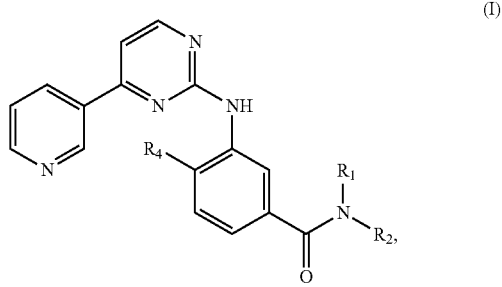

(I)

wherein $R_1$ represents hydrogen, lower alkyl, lower alkoxy-lower alkyl, acyloxy-lower alkyl, carboxy-lower alkyl, lower alkoxycarbonyl-lower alkyl or phenyl-lower alkyl;

$R_2$ represents hydrogen, lower alkyl, optionally substituted by one or more identical or different radicals $R_3$, cycloalkyl, benzcycloalkyl, heterocyclyl, an aryl group, or a mono- or bicyclic heteroaryl group comprising 0-, 1-, 2- or 3-ring nitrogen atoms and 0 or 1 oxygen atom and 0 or 1 sulfur atom, which groups in each case are unsubstituted or mono- or poly-substituted; and $R_3$ represents hydroxy, lower alkoxy, acyloxy, carboxy, lower alkoxycarbonyl, carbamoyl, N-mono- or N,N-disubstituted carbamoyl, amino, mono- or di-substituted amino, cycloalkyl, heterocyclyl, an aryl group, or a mono- or bi-cyclic heteroaryl group comprising 0-, 1-, 2- or 3-ring nitrogen atoms and 0 or 1 oxygen atom and 0 or 1 sulfur atom, which groups in each case are unsubstituted or mono- or poly-substituted, or $R_1$ and $R_2$, together, represent alkylene with 4, 5 or 6 carbon atoms optionally mono- or di-substituted by lower alkyl, cycloalkyl, heterocyclyl, phenyl, hydroxy, lower alkoxy, amino, mono- or di-substituted amino, oxo, pyridyl, pyrazinyl or pyrimidinyl; benzalkylene with 4 or 5 carbon atoms; oxaalkylene with 1 oxygen and 3 or 4 carbon atoms; or azaalkylene with 1 nitrogen and 3 or 4 carbon atoms wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N,N-disubstituted carbamoyl-lower alkyl, cycloalkyl, lower alkoxycarbonyl, carboxy, phenyl, substituted phenyl, pyridinyl, pyrimidinyl or pyrazinyl;

R₄ represents hydrogen, lower alkyl or halogen; and
a N-oxide or a pharmaceutically acceptable salt of such a compound for the preparation of a pharmaceutical composition for the treatment of FIP1L1-PDGFRα, or TEL-PDGFRβ-induced myeloproliferative diseases, especially for the curative and/or prophylactic treatment of myelomonocytic leukaemia, hypereosinophilic syndrome, chronic eosinophilic leukemia and hypereosinophilic syndrome with resistance to imatinib or myelomonocytic leukemia with resistance to imatinib.

The present invention further relates to use of compounds of formula (I) to treat or prevent myeloproliferative diseases induced by FIP1L1-PDGFRα or TEL-PDGFRβ especially for the curative and/or prophylactic treatment of myelomonocytic leukaemia, chronic eosinophilic leukemia, hypereosinophilic syndrome and hypereosinophilic syndrome with resistance to imatinib.

The general terms used hereinbefore and hereinafter preferably have within the context of this disclosure the following meanings, unless otherwise indicated:

The prefix "lower" denotes a radical having up to and including a maximum of 7 carbon atoms, especially up to and including a maximum of 4 carbon atoms, the radicals in question being either linear or branched with single or multiple branching.

Where the plural form is used for compounds, salts and the like, this is taken to mean also a single compound, salt or the like.

Any asymmetric carbon atoms may be present in the (R)-, (S)- or (R,S)-configuration, preferably in the (R)- or (S)-configuration. The compounds may thus be present as mixtures of isomers or as pure isomers, preferably as enantiomer-pure diastereomers.

The invention relates also to possible tautomers of the compounds of formula (I).

Lower alkyl is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or methyl. Preferably lower alkyl is methyl, propyl or tert-butyl.

Lower acyl is preferably formyl or lower alkylcarbonyl, in particular, acetyl.

An aryl group is an aromatic radical which is bound to the molecule via a bond located at an aromatic ring carbon atom of the radical. In a preferred embodiment, aryl is an aromatic radical having 6-14 carbon atoms, especially phenyl, naphthyl, tetrahydronaphthyl, fluorenyl or phenanthrenyl and is unsubstituted or substituted by 1 or more, preferably up to 3, especially 1 or 2 substituents, especially selected from amino, mono- or di-substituted amino, halogen, lower alkyl, substituted lower alkyl, lower alkenyl, lower alkynyl, phenyl, hydroxy, etherified or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenylthio, phenyl-lower alkylthio, lower alkylphenylthio, lower alkylsulfinyl, phenylsulfinyl, phenyl-lower alkylsulfinyl, lower alkylphenylsulfinyl, lower alkylsulfonyl, phenylsulfonyl, phenyl-lower alkylsulfonyl, lower alkylphenylsulfonyl, halogen-lower alkylmercapto, halogen-lower alkylsulfonyl, such as especially trifluoromethanesulfonyl, dihydroxybora (—B(OH)₂), heterocyclyl, a mono- or bi-cyclic heteroaryl group and lower alkylene dioxy bound at adjacent C-atoms of the ring, such as methylene dioxy. Aryl is more preferably phenyl, naphthyl or tetrahydronaphthyl, which in each case is either unsubstituted or independently substituted by 1 or 2 substituents selected from the group comprising halogen, especially fluorine, chlorine or bromine; hydroxy; hydroxy etherified by lower alkyl, e.g., by methyl, by halogen-lower alkyl, e.g., trifluoromethyl, or by phenyl; lower alkylene dioxy bound to two adjacent C-atoms, e.g., methylenedioxy, lower alkyl, e.g., methyl or propyl; halogen-lower alkyl, e.g., trifluoromethyl; hydroxy-lower alkyl, e.g., hydroxymethyl or 2-hydroxy-2-propyl; lower alkoxy-lower alkyl; e.g., methoxymethyl or 2-methoxyethyl; lower alkoxycarbonyl-lower alkyl, e.g., methoxycarbonylmethyl; lower alkynyl, such as 1-propynyl; esterified carboxy, especially lower alkoxycarbonyl, e.g., methoxycarbonyl, n-propoxy carbonyl or iso-propoxy carbonyl; N-mono-substituted carbamoyl, in particular, carbamoyl monosubstituted by lower alkyl, e.g., methyl, n-propyl or iso-propyl; amino; lower alkylamino, e.g., methylamino; di-lower alkylamino, e.g., dimethylamino or diethylamino; lower alkylene-amino, e.g., pyrrolidino or piperidino; lower oxaalkylene-amino, e.g., morpholino, lower azaalkylene-amino, e.g., piperazino, acylamino, e.g., acetylamino or benzoylamino; lower alkylsulfonyl, e.g., methylsulfonyl; sulfamoyl; or phenylsulfonyl.

A cycloalkyl group is preferably cyclopropyl, cyclopentyl, cyclohexyl or cycloheptyl, and may be unsubstituted or substituted by 1 or more, especially 1 or 2, substitutents selected from the group defined above as substitutents for aryl, most preferably by lower alkyl, such as methyl, lower alkoxy, such as methoxy or ethoxy, or hydroxy, and further by oxo or fused to a benzo ring, such as in benzcyclopentyl or benzcyclohexyl.

Substituted alkyl is alkyl as last defined, especially lower alkyl, preferably methyl; where 1 or more, especially up to 3, substituents may be present, primarily from the group selected from halogen, especially fluorine, amino, N-lower alkylamino, N,N-di-lower alkylamino, N-lower alkanoylamino, hydroxy, cyano, carboxy, lower alkoxycarbonyl, and phenyl-lower alkoxycarbonyl. Trifluoromethyl is especially preferred.

Mono- or di-substituted amino is especially amino substituted by 1 or 2 radicals selected independently of one another from lower alkyl, such as methyl; hydroxy-lower alkyl, such as 2-hydroxyethyl; lower alkoxy lower alkyl, such as methoxy ethyl; phenyl-lower alkyl, such as benzyl or 2-phenylethyl; lower alkanoyl, such as acetyl; benzoyl; substituted benzoyl, wherein the phenyl radical is especially substituted by 1 or more, preferably 1 or 2, substituents selected from nitro, amino, halogen, N-lower alkylamino, N,N-di-lower alkylamino, hydroxy, cyano, carboxy, lower alkoxycarbonyl, lower alkanoyl and carbamoyl; and phenyl-lower alkoxycarbonyl, wherein the phenyl radical is unsubstituted or especially substituted by 1 or more, preferably 1 or 2, substituents selected from nitro, amino, halogen, N-lower alkylamino, N,N-di-lower alkylamino, hydroxy, cyano, carboxy, lower alkoxycarbonyl, lower alkanoyl, and carbamoyl; and is preferably N-lower alkylamino, such as N-methylamino, hydroxy-lower alkylamino, such as 2-hydroxyethylamino or 2-hydroxypropyl, lower alkoxy lower alkyl, such as methoxy ethyl, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, or a substituent selected from the group comprising benzoylamino and phenyl-lower alkoxycarbonylamino, wherein the phenyl radical in each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl, carbamoyl or aminocarbonylamino. Di-substituted amino is also lower alkylene-amino, e.g., pyrrolidino, 2-oxopyrrolidino or piperidino; lower oxaalkylene-amino, e.g., morpholino, or lower azaalkylene-amino, e.g., piperazino or N-substituted piperazino, such as N-methylpiperazino or N-methoxycarbonylpiperazino.

Halogen is especially fluorine, chlorine, bromine, or iodine, especially fluorine, chlorine or bromine.

Etherified hydroxy is especially $C_8$-$C_{20}$alkyloxy, such as n-decyloxy, lower alkoxy (preferred), such as methoxy, ethoxy, isopropyloxy, or tert-butyloxy, phenyl-lower alkoxy, such as benzyloxy, phenyloxy, halogen-lower alkoxy, such as trifluoromethoxy, 2,2,2-trifluoroethoxy or 1,1,2,2-tetrafluoroethoxy, or lower alkoxy which is substituted by mono- or bi-cyclic heteroaryl comprising 1 or 2 nitrogen atoms, preferably lower alkoxy which is substituted by imidazolyl, such as 1H-imidazol-1-yl, pyrrolyl, benzimidazolyl, such as 1-benzimidazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, indolyl or thiazolyl.

Esterified hydroxy is especially lower alkanoyloxy; benzoyloxy; lower alkoxycarbonyloxy, such as tert-butoxycarbonyloxy; or phenyl-lower alkoxycarbonyloxy, such as benzyloxycarbonyloxy.

Esterified carboxy is especially lower alkoxycarbonyl, such as tert-butoxycarbonyl, iso-propoxycarbonyl, methoxycarbonyl or ethoxycarbonyl, phenyl-lower alkoxycarbonyl or phenyloxycarbonyl.

Alkanoyl is primarily alkylcarbonyl, especially lower alkanoyl, e.g., acetyl.

N-Mono- or N,N-disubstituted carbamoyl is especially substituted by 1 or 2 substituents independently selected from lower alkyl, phenyl-lower alkyl and hydroxy-lower alkyl, or lower alkylene, oxa-lower alkylene or aza-lower alkylene optionally substituted at the terminal nitrogen atom.

A mono- or bi-cyclic heteroaryl group comprising 0-, 1-, 2- or 3-ring nitrogen atoms and 0 or 1 oxygen atom and 0 or 1 sulfur atom, which groups in each case are unsubstituted or mono- or poly-substituted, refers to a heterocyclic moiety that is unsaturated in the ring binding the heteroaryl radical to the rest of the molecule in formula (I) and is preferably a ring, where in the binding ring, but optionally also in any annealed ring, at least 1 carbon atom is replaced by a heteroatom selected from the group consisting of nitrogen, oxygen and sulfur; where the binding ring preferably has 5- to 12-ring atoms, more preferably 5- or 6-ring atoms; and which may be unsubstituted or substituted by 1 or more, especially 1 or 2, substitutents selected from the group defined above as substitutents for aryl, most preferably by lower alkyl, such as methyl, lower alkoxy, such as methoxy or ethoxy, or hydroxy. Preferably the mono- or bi-cyclic heteroaryl group is selected from 2H-pyrrolyl, pyrrolyl, imidazolyl, benzimidazolyl, pyrazolyl, indazolyl, purinyl, pyridyl, pyrazinyl, pyrimidinyl, pyridazinyl, 4H-quinolizinyl, isoquinolyl, quinolyl, phthalazinyl, naphthyridinyl, quinoxalyl, quinazolinyl, quinnolinyl, pteridinyl, indolizinyl, 3H-indolyl, indolyl, isoindolyl, oxazolyl, isoxazolyl, thiazolyl, isothiazolyl, triazolyl, tetrazolyl, furazanyl, benzo[d]pyrazolyl, thienyl and furanyl. More preferably, the mono- or bi-cyclic heteroaryl group is selected from the group consisting of pyrrolyl; imidazolyl, such as 1H-imidazol-1-yl; benzimidazolyl, such as 1-benzimidazolyl; indazolyl, especially 5-indazolyl; pyridyl, especially 2-, 3- or 4-pyridyl; pyrimidinyl, especially 2-pyrimidinyl; pyrazinyl; isoquinolinyl, especially 3-isoquinolinyl; quinolinyl, especially 4- or 8-quinolinyl; indolyl, especially 3-indolyl; thiazolyl; benzo[d]pyrazolyl; thienyl; and furanyl. In one preferred embodiment of the invention, the pyridyl radical is substituted by hydroxy in ortho position to the nitrogen atom and hence exists at least partially in the form of the corresponding tautomer which is pyridin-(1H)-2-one. In another preferred embodiment, the pyrimidinyl radical is substituted by hydroxy both in position 2 and 4 and hence exists in several tautomeric forms, e.g., as pyrimidine-(1H,3H)2,4-dione.

Heterocyclyl is especially a 5-, 6- or 7-membered heterocyclic system with 1 or 2 heteroatoms selected from the group comprising nitrogen, oxygen and sulfur, which may be unsaturated or wholly or partly saturated, and is unsubstituted or substituted especially by lower alkyl, such as methyl; phenyl-lower alkyl, such as benzyl, oxo or heteroaryl, such as 2-piperazinyl; heterocyclyl is especially 2- or 3-pyrrolidinyl, 2-oxo-5-pyrrolidinyl, piperidinyl, N-benzyl-4-piperidinyl, N-lower alkyl-4-piperidinyl, N-lower alkyl-piperazinyl, morpholinyl, e.g., 2- or 3-morpholinyl, 2-oxo-1H-azepin-3-yl, 2-tetrahydrofuranyl or 2-methyl-1,3-dioxolan-2-yl.

Salts are especially the pharmaceutically acceptable salts of compounds of formula (I).

Such salts are formed, e.g., as acid addition salts, preferably with organic or inorganic acids, from compounds of formula (I) with a basic nitrogen atom, especially the pharmaceutically acceptable salts. Suitable inorganic acids are, e.g., halogen acids, such as hydrochloric acid, sulfuric acid or phosphoric acid. Suitable organic acids are, e.g., carboxylic, phosphonic, sulfonic or sulfamic acids, e.g., acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethane-sulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid; or other organic protonic acids, such as ascorbic acid.

In the presence of negatively charged radicals, such as carboxy or sulfo, salts may also be formed with bases, e.g., metal or ammonium salts, such as alkali metal or alkaline earth metal salts, e.g., sodium, potassium, magnesium or calcium salts; or ammonium salts with ammonia or suitable organic amines, such as tertiary monoamines, e.g., triethylamine or tri(2-hydroxyethyl)amine; or heterocyclic bases, e.g., N-ethyl-piperidine or N,N'-dimethylpiperazine.

When a basic group and an acid group are present in the same molecule, a compound of formula (I) may also form internal salts.

For isolation or purification purposes it is also possible to use pharmaceutically unacceptable salts, e.g., picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, e.g., in the purification or identification of the novel compounds, any reference to the free compounds hereinbefore and hereinafter is to be understood as referring also to the corresponding salts, as appropriate and expedient.

Compounds within the scope of formula (I) and the process for their manufacture are disclosed in WO 04/005281 published on Jan. 15, 2004 which is hereby incorporated into the present application by reference. A preferred compound is 4-methyl-3-[[4-(3-pyridinyl)-2-pyrimidinyl]amino]-N-[5-(4-methyl-1H-imidazol-1-yl)-3-(trifluoromethyl)phenyl] benzamide and N-oxides and pharmaceutically acceptable salts thereof of formula (II):

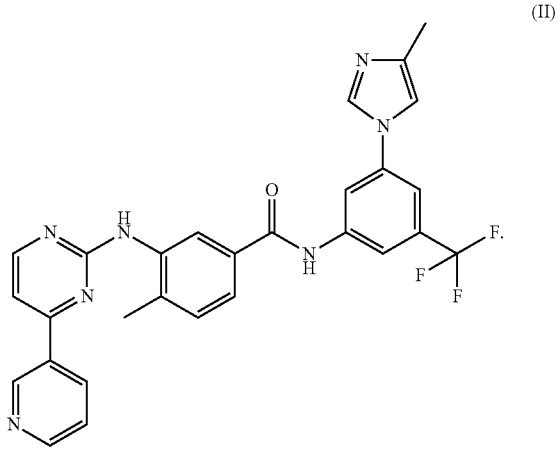 [SMILES: Cc1cn(-c2cc(NC(=O)c3ccc(C)c(Nc4nccc(-c5cccnc5)n4)c3)cc(C(F)(F)F)c2)cn1]

In each case where citations of patent applications or scientific publications are given in particular for the PYRIMIDYLAMINOBENZAMIDE DERIVATIVE compounds, the subject-matter of the final products, the pharmaceutical preparations and the claims are hereby incorporated into the present application by reference to these publications.

The structure of the active agents identified by code nos., generic or trade names may be taken from the actual edition of the standard compendium "The Merck Index" or from databases, e.g., Patents International, e.g., IMS World Publications. The corresponding content thereof is hereby incorporated by reference.

It has now surprisingly been found that PYRIMIDYLAMINOBENZAMIDE DERIVATIVES possesses therapeutic properties, which render it particularly useful as to treat non-cancerous, benign brain tumors, especially neurofibromastosis.

The present invention thus concerns the use of PYRIMIDYLAMINOBENZAMIDE DERIVATIVES for the preparation of a drug for the treatment of non-cancerous, benign brain tumors, especially neurofibromastosis.

The present invention more particularly concerns the use of PYRIMIDYLAMINOBENZAMIDE DERIVATIVES for the preparation of a drug for the treatment of non-cancerous, benign brain tumors, especially neurofibromastosis.

In another embodiment, the instant invention provides a method for treating non-cancerous, benign brain tumors, especially NF comprising administering to a mammal in need of such treatment a therapeutically effective amount of PYRIMIDYLAMINOBENZAMIDE DERIVATIVES, or pharmaceutically acceptable salts or prodrugs thereof.

Preferably the instant invention provides a method for treating mammals, especially humans, suffering from non-cancerous, benign brain tumors, especially NF comprising administering to a mammal in need of such treatment an inhibiting amount of 4-methyl-3-[[4-(3-pyridinyl)-2-pyrimidinyl]amino]-N-[5-(4-methyl-1H-imidazol-1-yl)-3-(trifluoromethyl)phenyl]benzamide (Compound (II)) or a pharmaceutically acceptable salt thereof.

Preferably, this method is used for treating NF1 or NF2.

In another embodiment, the instant invention relates to the use of PYRIMIDYLAMINOBENZAMIDE DERIVATIVES for the preparation of a pharmaceutical composition for use in treating non-cancerous, benign brain tumors, especially NF.

In the present description, the term "treatment" includes both prophylactic or preventative treatment, as well as curative or disease suppressive treatment, including treatment of patients at risk of contracting the disease or suspected to have contracted the disease, as well as ill patients. This term further includes the treatment for the delay of progression of the disease.

The term "curative", as used herein, means efficacy in treating ongoing episodes involving non-cancerous, benign brain tumors, especially NF.

The term "prophylactic" means the prevention of the onset or recurrence of diseases involving non-cancerous, benign brain tumors, especially NF.

The term "delay of progression", as used herein, means administration of the active compound to patients being in a pre-stage or in an early phase of the disease to be treated, in which patients, e.g., a pre-form of the corresponding disease is diagnosed or which patients are in a condition, e.g., during a medical treatment or a condition resulting from an accident, under which it is likely that a corresponding disease will develop.

This unforeseeable range of properties means that the use of PYRIMIDYLAMINOBENZAMIDE DERIVATIVES are of particular interest for the manufacture of a medicament for the treatment of non-cancerous, benign brain tumors, especially NF.

To demonstrate that PYRIMIDYLAMINOBENZAMIDE DERIVATIVES are particularly suitable for the treatment of non-cancerous, benign brain tumors, especially NF with good therapeutic margin and other advantages, clinical trials can be carried out in a manner known to the skilled person.

The precise dosage of PYRIMIDYLAMINOBENZAMIDE DERIVATIVES to be employed for inhibiting non-cancerous, benign brain tumors, especially NF depends upon several factors including the host, the nature and the severity of the condition being treated, the mode of administration. The compound of formula (I) can be administered by any route including orally, parenterally, e.g., intraperitoneally, intravenously, intramuscularly, subcutaneously, intratumorally, or rectally, or enterally. Preferably, the compound of formula (I) is administered orally, preferably at a daily dosage of 1-300 mg/kg body weight or, for most larger primates, a daily dosage of 50-5000 mg, preferably 500-3000 mg. A preferred oral daily dosage is 1-75 mg/kg body weight or, for most larger primates, a daily dosage of 10-2000 mg, administered as a single dose or divided into multiple doses, such as twice daily dosing.

Usually, a small dose is administered initially and the dosage is gradually increased until the optimal dosage for the host under treatment is determined. The upper limit of dosage is that imposed by side effects and can be determined by trial for the host being treated.

Compounds of formula (I) may be combined with one or more pharmaceutically acceptable carriers and, optionally, one or more other conventional pharmaceutical adjuvants and administered enterally, e.g., orally, in the form of tablets, capsules, caplets, etc. or parenterally, e.g., intraperitoneally or intravenously, in the form of sterile injectable solutions or suspensions. The enteral and parenteral compositions may be prepared by conventional means.

The PYRIMIDYLAMINOBENZAMIDE DERIVATIVES can be used alone or combined with at least one other pharmaceutically active compound for use in these pathologies.

These active compounds can be combined in the same pharmaceutical preparation or in the form of combined preparations "kit of parts" in the sense that the combination partners can be dosed independently or by use of different fixed combinations with distinguished amounts of the combination partners, i.e., simultaneously or at different time points. The parts of the kit of parts can then, e.g., be administered simultaneously or chronologically staggered, that is at different time points and with equal or different time intervals for any part of the kit of parts. Non-limiting examples of compounds which can be cited for use in combination with PYRIMIDYLAMINOBENZAMIDE DERIVATIVES are cytotoxic chemotherapy drugs, such as cytosine arabinoside, daunorubicin, doxorubicin, cyclophosphamide, VP-16 or imatinib etc. Further, PYRIMIDYLAMINOBENZAMIDE DERIVATIVES could be combined with other inhibitors of signal transduction or other oncogene-targeted drugs with the expectation that significant synergy would result.

The invention further pertains the combination of a PYRIMIDYLAMINOBENZAMIDE DERIVATIVE as described hereinbefore with imatinib for the treatment of the diseases and conditions described hereinbefore. The administration of such a combination may be affected at the same time, i.e., in the form of a fixed, combined pharmaceutical composition or preparation, or sequentially or timely staggered. The administration of a PYRIMIDYLAMINOBENZAMIDE DERIVATIVE in a dosage form as described hereinbefore and of imatinib in its marketed form of GLEEVEC® in the U.S./GLIVEC® in Europe and with the dosages envisaged for these dosage forms is currently preferred.

The treatment of non-cancerous, benign brain tumors, especially NF with the above combination may be a so-called first line treatment, i.e., the treatment of a freshly-diagnosed disease without any preceeding chemotherapy or the like, or it may also be a so-called second line treatment, i.e., the treatment of the disease after a preceeding treatment with imatrinib or a PYRIMIDYLAMINOBENZAMIDE DERIVATIVE, depending on the severity or stage of the disease, as well as the over all condition of the patient, etc.

EXAMPLE I

The efficacy of the compounds of formula I as inhibitors of c-Kit and PDGF-R tyrosine kinase activity can be demonstrated as follows:

BaF3-Tel-PDGFRbeta and BaF3-KitD816V are BaF3 murine proB-cell lymphoma cell derivatives [the BaF3 cell line is available from the German Collection of Microorganisms and Cell Cultures (DSMZ), Braunschweig, Germany] that have been rendered IL-3-independent by stable transduction with Tel-fusion-activated PDGFβ-R wild-type (Golub T. R. et al., Cell 77(2): 307-316, 1994) or D816V-mutation-activated c-kit, respectively. Cells are cultured in RPMI-1640 (Animed #1-14F01-I) supplemented with 2% L-glutamine (Animed #5-10K50-H) and 10% fetal calf serum (FCS, Animed #2-01F16-I). Wild-type, untransfected BaF3 cells are maintained in above medium plus 10 U/ml IL-3 (mouse Interleukin-3, Roche #1380745).

Cells are diluted in fresh medium to a final density of $3 \times 10^5$ cells per ml and 50 µl aliquots seeded into 96-well plates ($1.5 \times 10^4$ cells per well). 50 µl 2× compound solutions are added. As internal control, the kinase inhibitor PKC412 is routinely used. Control cells treated with DMSO (0.1% final concentration) serve as growth reference (set as 100% growth). In addition, a plate blank value is routinely determined in a well containing only 100 µl of medium and no cells. $IC_{50}$ determinations are performed based on eight 3-fold serial dilutions of the test compound, starting at 10 µM. Following incubation of the cells for 48 h at 37° C. and 5% $CO_2$, the effect of inhibitors on cell viability is assessed by the resazurin sodium salt dye reduction assay (commercially known as AlamarBlue assay) basically as previously described (O'Brien J. et al., Eur. J. Biochem. 267: 5421-5426, 2000). 10 µl of AlamarBlue is added per well and the plates incubated for 6 h at 37° C. and 5% $CO_2$. Thereafter, fluorescence is measured using a Gemini 96-well plate reader (Molecular Devices) with the following settings: Excitation 544 nm and Emission 590 nm. Acquired raw data are exported to Excel-file format. For data analysis, the plate blank value is subtracted from all data points. The anti-proliferative effect of a compound by the AlamarBlue read-out was then calculated as percentage of the value of the control cells set as 100%. $IC_{50}$ values are determined using XLfit software program. The compounds of formula I show an $IC_{50}$ for c-Kit and PDGFβ-R in the range of 0.0003 to 20 µM, especially between 0.001 and 0.1 µM.

EXAMPLE 2

The human KIT gene encoding aa 544-976 was cloned into the baculovirus donor plasmid pFB-GST-01. This coding sequence was excised using restriction endonucleases Bam H1 and EcoR1 and ligated to a Bac-to-Bac donor vector pFB-GEX-P1 with compatible ends. Subsequently the desired mutations were brought into the KIT gene (by Dr. M Heinrich). Due to a frame shift within the original plasmid that was used to generate the mutant coding sequences, the mutated plasmid inserts were excised and inserted into the Bac-to-Bac donor vector pFB-GST-01 using the restriction enzymes BamH1-EcoR1 for each mutant. Automated sequencing confirmed the correct sequence to be present for each mutant plasmid.

Bacmid DNA was generated from 10 colonies each of DH10Bac cells transformed with pFB-G01-KIT-mutant plasmid clones as described in materials and methods and these transfected into Sf9 cells. The transfected cells were pelleted and the resultant recombinant baculovirus present in the supernatant medium amplified. Western blotting was applied to the lysed cell pellets to confirm the expression of the GST-c-KIT fusion protein by the viral clones using anti-KIT and anti-GST antibodies for immonudetection.

| Kit Mutation | Compound II $IC_{50}$ (µM) (avg) |
|---|---|
| D816F | >10 |
| D816H | >10 |
| D816N | <10 |
| D816Y | >10 |
| D816V | >10 |
| K642E | <10 |
| Y823D | <1 |
| Del 550-558 | <2 |
| Del 557-561 | <2 |
| N822K | <10 |
| V654A | >10 |
| N822H | <10 |
| Del 550-558 + V654A | <10 |
| Del 557-561 + V654A | >10 |

Virus containing media was collected from the transfected cell culture and used for infection to increase its titer. Virus containing media obtained after two rounds of infection was used for large-scale protein expression. For large-scale protein expression 100 cm² round tissue culture plates were seeded with 5×10⁷ cells/plate and infected with 1 mL of virus-containing media (approximately 5 MOIs). After 3 days, the cells were scraped off the plate and centrifuged at 500 rpm for 5 minutes. Cell pellets from 10-20, 100 cm² plates, were re-suspended in 50 mL of ice-cold lysis buffer (25 mM Tris-HCl, pH 7.5, 2 mM EDTA, 1% NP-40, 1 mM DTT, 1 mM PMSF). The cells were stirred on ice for 15 minutes and then centrifuged at 5000 rpm for 20 minutes.

The centrifuged cell lysate was loaded onto a 2 mL glutathione-sepharose column (Pharmacia) and washed 3× with 10 mL of 25 mM Tris-HCl, pH 7.5, 2 mM EDTA, 1 mM DTT, 200 mM NaCl. The GST-tagged proteins were then eluted by 10 applications (1 mL each) of 25 mM Tris-HCl, pH 7.5, 10 mM reduced-glutathione, 100 mM NaCl, 1 mM DTT, 10% glycerol and stored at −70° C.

The protein kinase activities of the various Kit mutants 200-500 ng were assayed in the presence or absence of inhibitors, 20 mM Tris-HCl, pH 7.6, 3 mM MnCl$_2$, 3 mM MgCl$_2$, 1 mM DTT, 10 μM Na$_3$VO$_4$, 3 μg/mL poly(Glu,Tyr) 4:1, 1% DMSO, 1.5 μM ATP (γ-[$^{33}$P]-ATP 0.1 μCi). The assay (30 μL) was carried out in 96-well plates at ambient temperature for 30 minutes and the reaction terminated by the addition of 20 μL of 125 mM EDTA. Subsequently, 30μ of the reaction mixture were transferred onto Immobilon-PVDF membrane (Millipore, Bedford, Mass., USA) previously soaked for 5 minutes with methanol, rinsed with water, then soaked for 5 minutes with 0.5% H$_3$PO$_4$ and mounted on vacuum manifold with disconnected vacuum source. After spotting all samples, vacuum was connected and each well rinsed with 200 μL 0.5% H$_3$PO$_4$. Membranes were removed and washed 4× on a shaker with 1.0% H$_3$PO$_4$, once with ethanol. Membranes were counted after drying at ambient temperature, mounting in Packard TopCount 96-well frame, and addition of 10 μL/well of Microscint (Packard). IC$_{50}$ values were calculated by linear regression analysis of the percentage inhibition in duplicate, at 4 concentrations (usually 0.01, 0.1, 1 and 10 μM). One unit of protein kinase activity is defined as 1 nmole of $^{33}$P transferred from [γ$^{33}$P]ATP to the substrate protein/minute/mg of protein at RT.

I claim:

1. A method for treating neurofibromatosis type 1 or type 2 in a patient suffering from non-cancerous, benign brain tumors, comprising the step of administering to the patient a therapeutically effective amount of 4-methyl-3-[[4-(3-pyridinyl)-2-pyrimidinyl]amino]-N-[5-(4-methyl-1H-imidazol-1-yl)-3-(trifluoromethyl)phenyl]benzamide of formula (II):

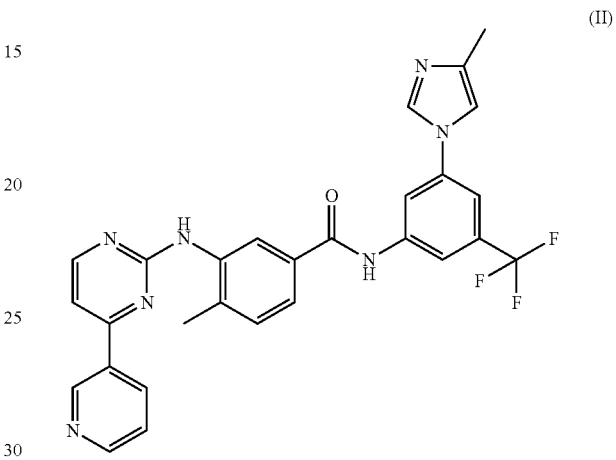

as a hydrochloride salt.

2. The method according to claim 1 wherein the daily dosage is 10-2000 mg.

* * * * *